(12) United States Patent
Halperin

(10) Patent No.: US 7,767,791 B2
(45) Date of Patent: Aug. 3, 2010

(54) METHODS, PRODUCTS AND TREATMENTS FOR DIABETES

(75) Inventor: Jose Halperin, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 169 days.

(21) Appl. No.: 11/413,130

(22) Filed: Apr. 27, 2006

(65) Prior Publication Data

US 2006/0257936 A1 Nov. 16, 2006

Related U.S. Application Data

(63) Continuation of application No. 10/833,581, filed on Apr. 28, 2004, now Pat. No. 7,049,082, which is a continuation of application No. 09/835,752, filed on Apr. 16, 2001, now Pat. No. 6,835,545.

(60) Provisional application No. 60/203,254, filed on May 8, 2000.

(51) Int. Cl.
*C07K 16/00* (2006.01)
*G01N 33/53* (2006.01)

(52) U.S. Cl. ................. 530/387.1; 530/387.9; 530/868; 435/7.1; 435/975

(58) Field of Classification Search ........................ None
See application file for complete search history.

(56) References Cited

U.S. PATENT DOCUMENTS

| 4,281,061 | A | 7/1981 | Zuk et al. |
|---|---|---|---|
| 4,816,567 | A | 3/1989 | Cabilly et al. |
| 5,225,539 | A | 7/1993 | Winter |
| 5,470,759 | A | 11/1995 | Sugiyama et al. |
| 5,585,089 | A | 12/1996 | Queen et al. |
| 5,693,762 | A | 12/1997 | Queen et al. |
| 5,789,208 | A | 8/1998 | Sharon |
| 5,853,703 | A | 12/1998 | Cerami et al. |
| 5,859,205 | A | 1/1999 | Adair et al. |
| 6,835,545 | B2 | 12/2004 | Halperin |
| 7,049,082 | B2 | 5/2006 | Halperin |
| 2004/0219606 | A1 | 11/2004 | Halperin |
| 2005/0032128 | A1 | 2/2005 | Halperin |

FOREIGN PATENT DOCUMENTS

| EP | 0394035 | 10/1990 |
|---|---|---|
| EP | 1789449 | 5/2007 |
| WO | WO 98/19711 | 5/1998 |
| WO | WO 2004/106941 | 12/2004 |
| WO | WO 2006/009533 A | 1/2006 |
| WO | WO 2006/086098 A2 | 8/2006 |

OTHER PUBLICATIONS

Acosta, et al., Molecular basis for a link between complement and the vascular complications of diabetes. Proc Natl Acad Sci 97: 5450-5455, 2000.

Benzaquen, et al., Terminal complement proteins C5b-9 release basic fibroblast growth factor and platelet-derived growth factor from endothelial cells. J. Exp. Med. 179: 985-992, 1994.

Davies, et al., CD59, an LY-6-like protein expressed in human lymphoid cells, regulates the action of the complement membrane attack complex on homologous cells. J. Exp. Med., 170(3): 637-654, 1989.

Fletcher, et al., Structure of a soluble, glycosylated form of the human complement regulatory protein CD59. Structure, 2: 185-199, 1994.

Halperin, et al., Terminal complement complex C5b-9 stimulates mitogenesis in 3T3 cells. J. Clin. Invest., 91: 1974-1978, 1993.

Halperin, et al., Properties of the Na+-K+ pump in human red cells with increased number of pump sites. J. Clin. Invest., 80: 128-137, 1987.

Halperin, et al., Transient changes in erythrocyte membrane permeability are induced by sublytic amounts of the complement membrane attack complex (C5b-9). Blood 81: 200-205, 1993.

Hughes, et al., Isolation and characterization of a membrane protein from rat erythrocytes which inhibits lysis by the membrane attack complex of rat complement. Biochem. J., 284: 169-176, 1992.

Myint, et al., Immunological detection of glycated proteins in normal and streptozotocin-induced diabetic rats using anti hexitol-lysine IgG. Biochem. Biophys. Acta 1272: 73-79, 1995.

Philbrick, et al., The CD59 antigen is a structural homologue of murine Ly-6 antigens but lacks interferon inducibility. Eur. J. Immunol., 20: 87-92, 1990.

Rosoklija, et al., Local activation of the complement system in endoneurial microvessels of diabetic neuropathy. Acta Neuro. 99: 55-62, 2000.

Van Den Berg, et al., The sheep analogue of human CD59: purification and characterization of its complement inhibitory activity. Immunology 78: 349-357, 1993.

Zhao, et al., Amplified gene expression in CD59-transfected Chinese hamster ovary cells confers protection against the membrane attack complex of human complement. J. Biol. Chem. 266: 13418-13422, 1991.

Zhang, J. et al., Early Complement Activation and Decreased Levels Of Glycosylphosphatidylinositol-Anchored Complement Inhibitors in Human and Experimental Diabetic Retinopathy. Diabetes, 51: 3499-3504, 2002.

Qin, X. et al., A Role of Glycated Human Cd59 and the Complement System in the Pathogenesis of Chronic Vascular Complications of Diabetes. International Immunopharmacology, 2: 1382-1383, 2002.

Qin X. et al., Genomic Structure, Functional Comparison, and Tissue Distribution Of Mouse Cd59a and Cd59b. Mammalian Genome, 12: 582-589, 2001.

(Continued)

*Primary Examiner*—David A. Saunders
*Assistant Examiner*—F. Pierre VanderVegt
(74) *Attorney, Agent, or Firm*—Wolf, Greenfield & Sacks, P.C.

(57) ABSTRACT

The invention involves assays, diagnostics, kits, and assay components for determining levels of K41-glycated CD59 in subjects. Treatments for subjects based upon levels of K41-glycated CD59 also are provided.

13 Claims, 5 Drawing Sheets

OTHER PUBLICATIONS

Acosta et al., Complement and complement regulatory proteins as potential molecular targets for vascular diseases. Current Pharmaceutical Design, 2004;10:1-9.

Bodian et al., Mutational analysis of the active site and antibody epitopes of the complement-inhibitory glycoprotein, CD59. J Exp Med. Feb. 3, 1997;185(3):507-16.

Harlow et al., Antibodies: A Laboratory Manual. 1998;321-323.

Lapolla et al., The role of mass spectrometry in the study of non-enzymatic protein glycation in diabetes. Mass Spectrom Rev. Sep.-Oct. 2000;19(5):279-304. Review.

Suzuki et al., Immunofluorescence staining of renal biopsy samples in patients with diabetic nephropathy in non-insulin-dependent diabetes mellitus using monoclonal antibody to reduced glycated lysine. J Diabetes Complications. Nov.-Dec. 1996;10(6):314-9.

Takata et al., Glycated Cu,Zn-superoxide dismutase in rat lenses: evidence for the presence of fragmentation in vivo. Biochem Biophys Res Commun. Feb. 6, 1996;219(1):243-8.

Walton, et al., Synthesis of N-(1-Deoxyhexito1-1-YL) Amino Acids, Reference Compounds for the Nonenzymic Glycosylation of Proteins, Carbohydrate Research, 128: 37-49, 1984.

International Search Report —PCT/US2008/005831 —Filed Jul. 5, 2008.

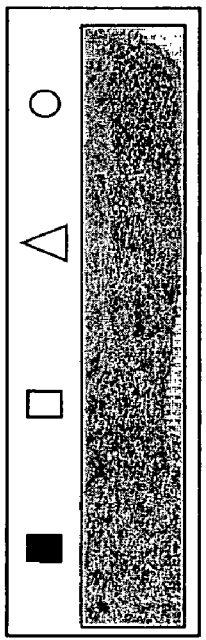
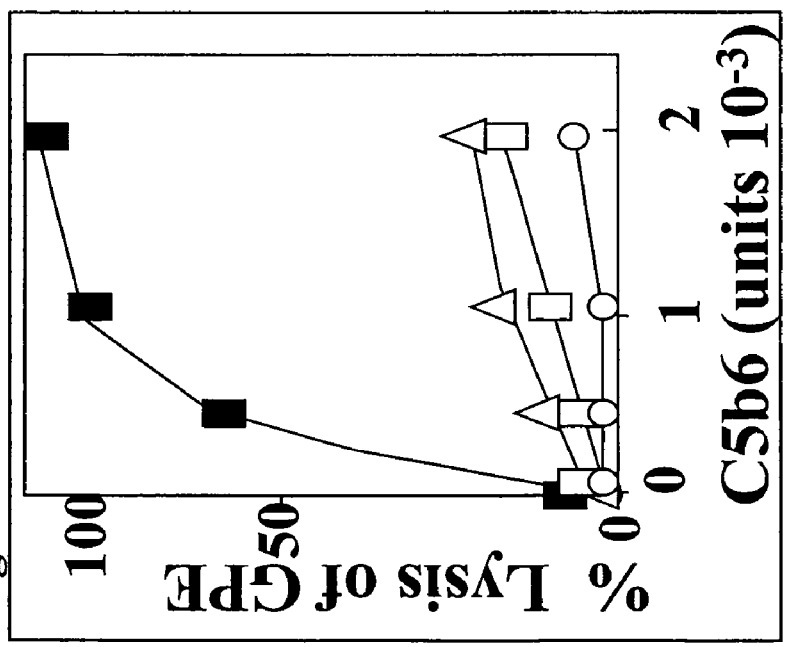
Fig. 3A
Fig. 3B
Fig. 3C

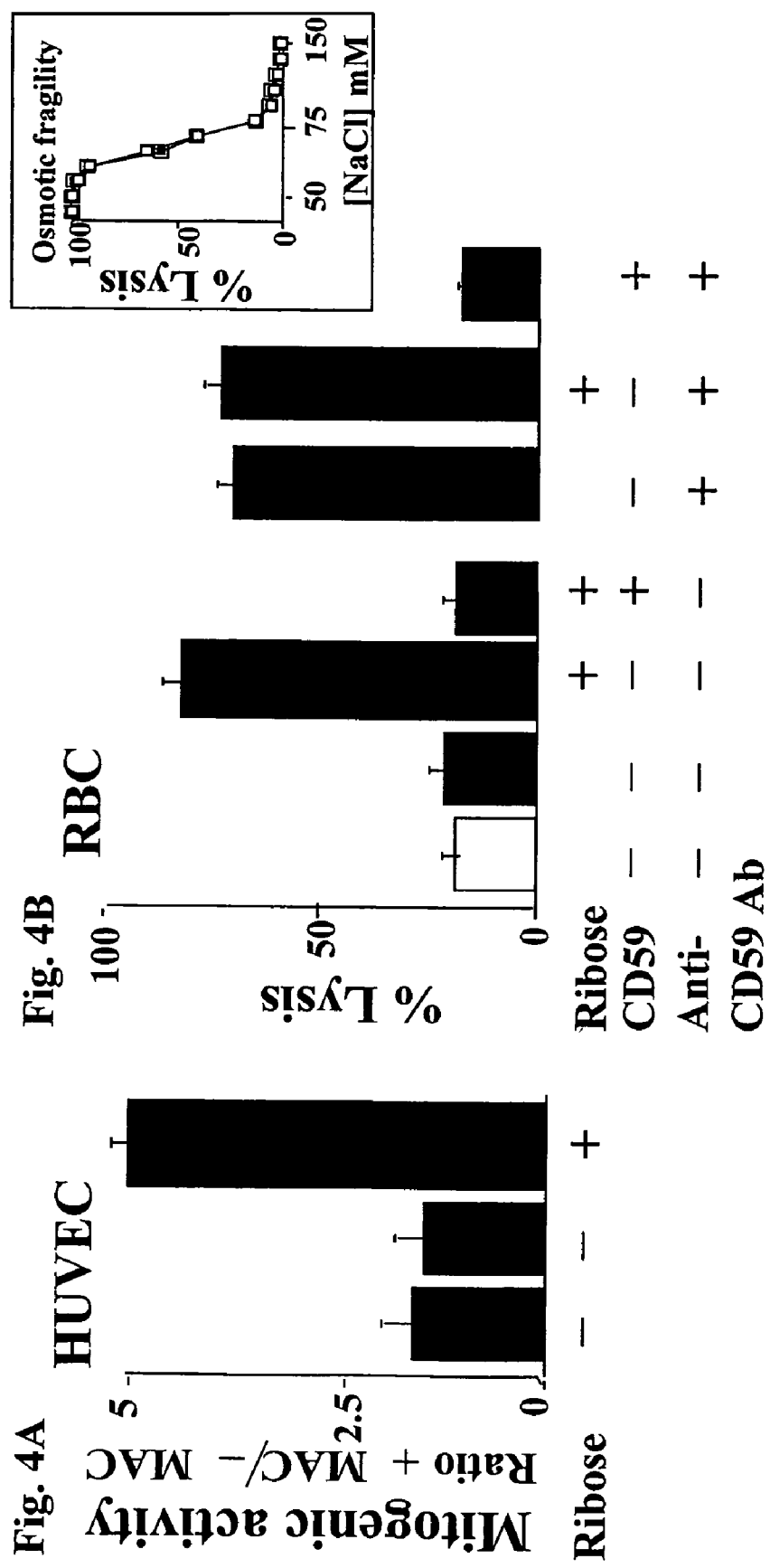

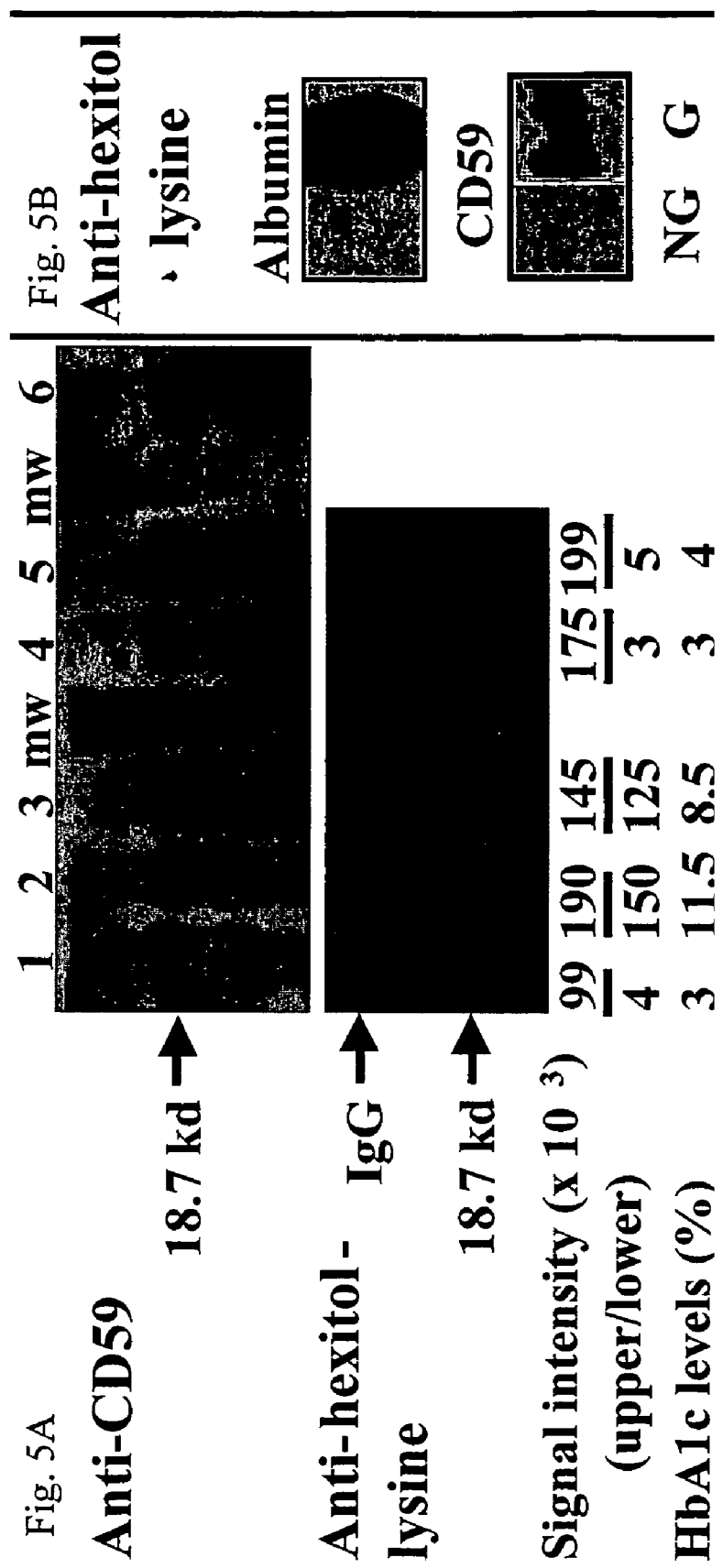

METHODS, PRODUCTS AND TREATMENTS FOR DIABETES

RELATED APPLICATION

This application is a continuation of application Ser. No. 10/833,581, filed on Apr. 28, 2004, which is a continuation of application Ser. No. 09/835,752, filed on Apr. 16, 2001, now issued as U.S. Pat. No. 6,835,545, which claims priority under 35 U.S.C. § 119 to U.S. Provisional Patent Application Ser. No. 60/203,254 filed May, 8, 2000, the entire contents each of which are incorporated by reference herein.

GOVERNMENT SUPPORT

This invention was made with government support under Grant No. DK052855 awarded by the National Institutes of Health. The government has certain rights in the invention.

BACKGROUND OF THE INVENTION

Diabetes Mellitus (diabetes) is a leading cause of morbidity and mortality in the adult population. This is primarily because diabetic patients tend to develop vascular complications that involve the kidneys (diabetic nephropathy), the retina (diabetic retinopathy), as well as large and small blood vessels in other organs (macro- and micro-vascular disease) including nerves (diabetic neuropathy). It is well established that the vascular complications of diabetes are caused by elevated blood glucose levels over long periods of time. Elevated blood glucose levels affect proteins by a process known as glycation. Different "glycated" proteins have been identified in diabetic subjects, including albumin, hemoglobin and others. Measurement of the extent of protein "glycation" of certain proteins is considered a valuable clinical tool to assess long term glycemic control and thereby the efficacy of diabetes treatment.

Glycation, the non-enzymatic attachment of glucose to proteins, is considered a major pathophysiological mechanism causing tissue damage in diabetic subjects. Glycation involves the reaction of glucose and/or other reducing sugars with amino groups in proteins resulting in the formation of a Schiff base or aldimine. This labile adduct can tautomerize via the Amadori rearrangement to the more stable ketoamine. The function of the glycated protein may be impaired, depending on the location of the amino group(s) affected. For example, amino-terminal glycation of the β-chains of hemoglobin gives rise to the glycated hemoglobins (HbAl) in which responsiveness to 2,3-diphosphoglycerate is decreased and oxygen affinity increased. Glycation of the major thrombin inhibitor of the coagulation system, antithrombin III, decreases its affinity for heparin, and has been postulated to contribute to the hypercoagulable state associated with diabetes.

Hemoglobin glycation and thrombin inhibitor glycation do not account for the vascular complications of diabetes. The mechanism which results in such complications remains unknown.

Currently, protein glycation in diabetic subjects is measured in blood by estimating the amount of glycated hemoglobin (hemoglobin A1c) through a complicated clinical test that requires extraction of a blood sample. Accordingly, there is a need for a simplified and less invasive method for rapid monitoring of protein glycation levels.

SUMMARY OF THE INVENTION

The glycation of the membrane protein known as CD59, a key regulator of the complement system, has been discovered, according to the invention, as being involved in the pathogenesis of the vascular complications of diabetes. Unexpectedly, glycated CD59 has now been identified in human urine. The amount of glycated CD59 in human urine correlates with glycemic control and levels of glycated hemoglobin. Detection of glycated CD59 in the urine of diabetic patients can be used to monitor glycemic control in diabetic patients, and to select subjects for therapy.

The invention, in one aspect, is a method of characterizing the impact of blood sugar levels on abnormal glycation levels in a subject. The method involves obtaining a level of the amount of K41-glycated CD59 from a sample obtained from the subject.

In one embodiment the method involves comparing the level of K41-glycated CD59 to a control. In one embodiment, the sample is a fluid sample. Preferred samples are urine and blood, most preferably, urine. In one embodiment the subject is diabetic.

The subject can be receiving treatment for regulating blood sugar levels.

In one embodiment the level of K41-glycated CD59 is obtained using an agent that binds CD59. Preferably, the agent binds specifically CD59. Most preferably, the agent binds specifically K41-glycated CD59. The level of K41-glycated CD59 can be obtained, for example, using an immunoassay.

The invention in another aspect is a method of evaluating a treatment for regulating blood sugar levels. The method includes obtaining a first level of the amount of K41-glycated CD59 from a first sample obtained from a subject undergoing the treatment for regulating blood sugar levels, and obtaining a second level of the amount of K41-glycated CD59 from a second sample obtained from the subject after obtaining the first level, and comparing the first level to the second level as an indication of evaluation of the treatment. Preferably, the second level is obtained at least one day after the first level. In important embodiments, the second level is a plurality of second levels spaced out over time so that long term treatment can be evaluated and monitored.

In one embodiment the subject is diabetic. The subject can be undergoing treatment with an oral blood sugar regulating agent. In another embodiment, the subject is undergoing treatment with insulin or an insulin analog.

The samples preferably are fluid samples. The samples can be urine or blood, preferably urine. In one embodiment the levels are obtained using an immunoassay.

The invention in another aspect involves a method of selecting a treatment for regulating blood sugar levels in a subject. The method includes obtaining a level of the amount of K41-glycated CD59 from a sample obtained from the subject, and selecting the treatment for regulating blood sugar levels in the subject based at least in part on the level obtained. In one embodiment the subject is diabetic. The subject can already be receiving drug therapy for regulating blood sugar levels. In another embodiment, the subject has not yet received drug therapy for regulating blood sugar levels.

Preferred embodiments, including samples and assays, are as described above.

Another aspect of the invention is a method for determining regression, progression or onset of a condition characterized by abnormal levels of glycated protein. The method involves obtaining a level of the amount of K41-glycated CD59 from a sample obtained from a subject, and comparing the level to a control as a determination of regression, progression or onset of the condition. The sample can be a fluid sample. Preferably, the fluid sample is blood or urine, most preferably urine.

The subject can be diabetic. In one embodiment, the subject is undergoing drug therapy for regulating blood sugar levels.

The level can be obtained using an agent that binds to K41-glycated CD59. Preferably, the agent binds specifically to K41-glycated CD59. In one embodiment the level is obtained using an immunoassay.

Another aspect of the invention is a method of treating a subject to reduce the risk of or the progression of a disorder associated with abnormally high levels of K41-glycated CD59. The method of treatment involves selecting and administering to a subject who is known to have an abnormally high level of K41-glycated CD59 an agent for reducing K41-glycated CD59 levels in an amount effective to reduce K41-glycated CD59 levels. In one embodiment the subject is diabetic. In one embodiment the agent is an oral blood sugar regulating agent and the subject is otherwise free of symptoms calling for any oral blood sugar regulating agent. In one embodiment the agent is insulin or an insulin analog and the subject is otherwise free of symptoms calling for treatment with insulin.

In one embodiment the subject already is being treated with a therapeutic for lowering blood sugar levels and the therapeutic is not the agent. In another embodiment the subject already is being treated with the agent in a previous amount and wherein the effective amount is a higher dose than the previous amount.

Another aspect of the invention is a composition of matter that is isolated K41-glycated CD59. In one embodiment the isolated K41-glycated CD59 represents at least 20%, 30%, 40%, 50%, 60%, 70%, 80%, 90% or 95% of CD59 in the composition.

Another aspect of the invention is a composition of matter that is pure K41-glycated CD59 or a fragment thereof, wherein the fragment comprises at least 8, 9, 10, 11, 12, 13, 14, 15, 16, 17, 18, 19, or 20 contiguous amino acids having a consecutive sequence found in CD59 and including K41, and wherein K41 is glycated.

Another aspect of the invention is an agent that binds specifically to K41-glycated CD59 but not to K41-nonglycated CD59. In one embodiment the agent is an antibody.

According to still another aspect of the invention, a kit is provided for determining the level of K41-glycated CD59 and a sample. The kit comprises a package containing (1) an agent that binds specifically to only one of K41-glycated CD59 and K41-nonglycated CD59, and (2) a control. In one embodiment, the agent is two agents, a first agent that binds both glycated and nonglycated CD59 and a second agent that binds only one of a glycated K41 and a nonglycated K41. Thus, the first agent can bind specifically CD59, without distinguishing K41-glycated and K41-nonglycated CD59, and the second agent may be capable of distinguishing a glycated and a nonglycated lysine motif. In a preferred embodiment, the agent binds specifically K41-glycated CD59 or K41 nonglycated CD59. In one preferred embodiment, the agent is an antibody or a fragment of an antibody. The kit may further comprise instructions for using the kit for any of the methods described above. In another embodiment, the agent is a first agent and the kit further comprises a second agent. The first agent binds specifically to K41-glycated CD59 and the second agent binds specifically to K41-nonglycated CD59.

These and other aspects of the invention will be described in greater detail below.

BRIEF DESCRIPTION OF THE DRAWINGS

FIG. 3A is an image of a western blot and FIGS. 3B and 3C are graphs. Panel (3A) indicates expression of wild-type (WT) CD59, and CD59 mutants Gln-41 and Gln-44 in CHO cells as confirmed by SDS-PAGE followed by Western blot analysis of CHO cell extracts using the YTH 53.1 monoclonal antibody, Vector (closed square); WT (open square); CD59-Gln-41 (open triangle); Gln-44 (open circle). Panel (3B) indicates activity of WT and mutant CD59s tested in the GPE hemolytic assay before and after glycation with ribose for the time intervals indicated. Panel (3C) indicates CD59 and mutant CD59 activity as a percent of control activity for a cell suspension of GPE incubated with purified WT CD59 (open squares) and Gln-41 (open triangles), and Gln-44 (open circles) following incubation with the glycating sugar ribose. Data points represent the mean of triplicate determinations (SEM are smaller than the data points). The figure is representative of experiments run three times with comparable results.

FIGS. 4A and 4B are bar graphs. Panel (4A) Bar graph indicating HUVEC incubated with or without 50 mM ribose followed by reduction with cyanoborohydride. Cells were then exposed to purified terminal complement components C5b6, C7, C8 and C9 to form the MAC and the mitogenic activity in the conditioned medium was measured. Results are expressed as the ratio of mitogenic activity released into the conditioned media in the presence or absence of MAC. Panel (4B). Indicates Human RBC incubated without or with 50 mM ribose followed by reduction with cyanoborohydride to stabilize labile Schiff base adducts. After volume adjustment, aliquots of glycated and non glycated cells were separated for rescue with purified CD59 (4 µg), exposure to neutralizing anti-CD59 antibody (YTH53.1) or both, and then exposed to purified C5b6, C7, C8 and C9 to form the MAC. Open columns represent control cells not exposed to cyanoborohydride, filled columns represent cells exposed to cyanoborohydride, as above.

FIGS. 5A and 5B are images of immunoblots. Panel (5A) is an immunoblot of urine samples from non-diabetic (lanes 1, 4 and 5) and diabetic (lanes 2 and 3) subjects. Urine was concentrated by ultrafiltration, separated by anion exchange chromatography and fractions dot-blotted for the presence of CD59 with anti-CD59 specific antibody. CD59-positive fractions were pooled and immunoprecipited with the HCl anti-CD59 specific antibody. The immunoprecipitate was separated by SDS-PAGE and immunoblotted. Panel (5A), upper blot: immunoblot of CD59 positive fractions of the immunoprecipitate with the monoclonal anti-CD59 YTH53.1. Lower blot: The immunoprecipitate separated by SDS-PAGE and immunoblotted with the anti-hexitol-lysine antibody. Lower section, Panel A indicates levels of glycated CD59 and glycated hemoglobin (HbAlc). Panel (5B). Immunoblot of glycated (G) and non-glycated (NG) albumin (left) and affinity chromatography purified CD59 (right) with anti-hexitol-lysine antibody.

DETAILED DESCRIPTION

Figure 1:
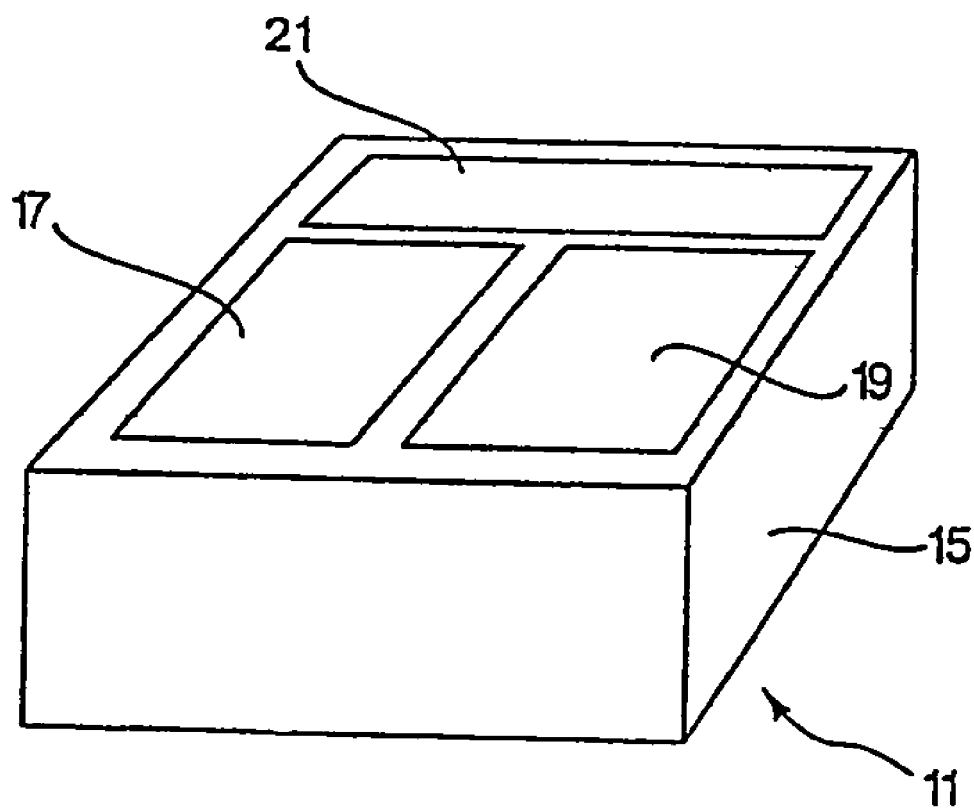
FIG. 1 is a schematic of a kit according to the invention.

The invention disclosed herein describes novel methods and compositions for detecting and measuring K41-glycated CD59 levels, particularly as they relate to glycemic levels. The discovery that CD59 is glycated facilitates analysis of diseases in which the amount of CD59 glycation differs from normal levels. For example, it has been discovered that the level of glycation of CD59 is elevated in diabetes. Thus, onset, progression and/or regression of diabetes or other diseases can be monitored by monitoring levels of glycated CD59 in a subject. It also has been determined that CD59 is present in urine. Therefore, the measurement can be done in urine without requiring a blood sample.

In addition, in contrast to markers of glycation such as hemoglobin, glycation of CD59 is believed to be involved in the pathogenesis of the vascular complications of diabetes. Accordingly, clinical evaluation of K41-glycated CD59 in urine is a direct measure for vascular damage induced by glycation. Without wishing to be bound by any particular theory, it is believed that patients with abnormally high levels of K41-glycated CD59 in urine will either have or will be more prone to develop vascular complications of diabetes.

As used herein, CD59 (also known as membrane inhibitor of reactive lysis [MIRL], protectin, HRF20 and H19) and K41-glycated CD59 are a polypeptide having substantial nucleotide and/or amino acid sequence identity of Accession No. M95708 (Davies, A., et al., Journal J. Exp. Med. 170(3), 637-654(1989)).

As used herein, "K41-glycated CD59" means CD59 which has been glycated at amino acid No. 41 of CD59, which is a lysine (hence K41). It has been determined, surprisingly, that K41-glycation of CD59 is correlated to abnormal blood sugar levels and that glycation at K41 interferes with the normal activity of CD59. CD59 functions normally by binding to the terminal components of the membrane attack complex of complement (MAC), thereby interfering with membrane insertion and polymerization of the C9 component of complement. Glycation at the K41 of CD59 interferes with CD59's ability to prevent the assembly of the MAC. It is believed that, as a result of K41-glycation of CD59, the MAC is permitted to be activated and leads to the development of proliferative chronic diabetic complications. Indeed, the present inventor has shown that the membrane attack complex stimulates proliferation of fibroblasts, smooth muscle, mesangial and other cells, in part by releasing growth factors such as FGF and PDGF from MAC-targeted endothelium. The MAC also induces increased synthesis of extracellular matrix proteins by mesangial cells. Thus, increased MAC deposition in diabetic tissues is believed to induce growth factor release from endothelium, which stimulates cell proliferation in the vascular wall and contributes to the expansion of the extracellular matrix and to the glomerulosclerosis that characterizes diabetic nephropathy.

Thus, according to one aspect of the invention, isolated K41-glycated CD59 is provided. By "isolated", it is meant separated from its native environment and present in sufficient quantity to permit its identification or use according to the procedures described herein. Isolated includes (1) selectively produced by expression cloning and glycation or (2) purified as by immunoprecipitation, chromatography or electrophoresis. Because an isolated material may be admixed with a carrier in a preparation, such as, for example, for injecting into an animal, the isolated material may comprise only a small percentage by weight of the preparation. The material is none-the-less isolated in that it has been separated from the substances with which it typically is associated in living systems, i.e. from K41-nonglycated CD59. According to the present invention, the isolated K41-glycated CD59 represents at least 10%, 20%, 30%, 40%, 50%, 60%, 70%, 80%, 90% or 95% of the CD59 in the composition (i.e. percentage of total CD59 both K41-glycated and K41-nonglycated).

According to another aspect of the invention, pure K41-glycated CD59 is provided. Isolated proteins or polypeptides may, but need not be, pure. The term "pure" means the proteins or polypeptides are essentially free of other substances with which they may be found in nature or in in vivo systems to an extent practical and appropriate for their intended use. Pure polypeptides may be produced by techniques well-known in the art. As used herein, "pure" means at least 95% of the total CD59 is K41-glycated CD59.

The invention also involves fragments of the foregoing proteins. A fragment of K41-glycated CD59 comprises at least 8, 9, 10, 11, 12, 13, 14, 15, 16, 17, 18, 19 or 20 contiguous amino acids of CD59 having a consecutive sequence found in CD59 and including K41, wherein K41 is glycated. Fragments of K41-glycated CD59 can be used for a variety of purposes, including in the preparation of molecules that bind specifically to K41-glycated CD59 and in immunoassays well-known to those of ordinary skill in the art, including competitive binding immunoassays. One such peptide comprises amino acids 36-50 of CD59, wherein the N-terminus and K38 are both blocked to prevent glycation at these points. Virtually any fragment, including the active site of CD59 is useful according to the invention. Fragments including (N-term) YNKAWKFEHANFNDC (C term) SEQ ID NO: 1 are particularly useful according to the invention for raising antibodies to glycated CD59. Thus, as will be apparent to those of ordinary skill in the art, fragments beginning anywhere from amino acid No. 1, 2, 3 . . . (to and including amino acid No. 36) and peptides ending at amino acid 50, 51, 52, 5 . . . (to and including amino acid 77) are particularly useful according to the invention, for human sequences. As is well-known to those of ordinary skill in the art, sequences of non-human subjects differ.

As mentioned above, by having isolated or pure material, or fragments thereof, agents can be prepared that bind specifically to K41-glycated CD59. As used herein, "binding specifically to" means capable of distinguishing the identified material from other materials sufficient for the purpose to which the invention relates. Thus, "binding specifically to" CD59 means the ability to bind to and distinguish CD59 from other proteins. Binding specifically to K41-glycated CD59 means binding to and distinguishing K41-glycated CD59 from K41-nonglycated CD59.

Agents that bind to CD59 molecules and/or K41-glycated CD59 molecules, and fragments thereof, include polypeptide agents. Such polypeptides include polyclonal and monoclonal antibodies, prepared according to conventional methodology. Antibodies that bind CD59 molecules and/or K41-glycated CD59 molecules and are useful for determining glycated CD59 levels, include but are not limited to: antibodies that bind specifically to CD59, antibodies that bind specifically to fragments of CD59, antibodies that bind specifically to K-glycated regions of proteins including CD59, and antibodies that bind specifically to K41-glycated CD59 or fragments of CD59. Certain antibodies useful in the methods of the invention already are known in the art and include anti-CD59 antibodies as well as anti-glycation-moiety antibodies, for example Anti-CD-59 YTH53.1, and the anti-hexitol-lysine antibody, which binds to glycated CD59. Agents that bind specifically K41-glycated CD59 but not K41-nonglycated CD59, and vice-versa, are believed novel and part of the present invention.

Significantly, as is well-known in the art, only a small portion of an antibody molecule, the paratrope, is involved in the binding of the antibody to its epitope (see, in general, Clark, W. R. (1986) *The Experimental Foundations of Modem Immunology*, Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F9ab').sub.2 fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd Fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (Frs), which maintain the tertiary structure of the paratope (see, in general, Clark, W. R. (1986) *The Experimental Foundations of Modem Immunology*, Wiley & Sons, Inc., New York; Roitt, I. (1991) *Essential Immunology*, 7th Ed., Blackwell Scientific Publications, Oxford). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. See, e.g., U.S. Pat. Nos. 4,816,567, 5,225,539, 5,585,089, 5,693,762 and 5,859,205.

Thus, for example, PCT International Publication Number WO 92/04381 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies.

Thus, as will be apparent to one of ordinary skill in the art, the present invention also provides for F(ab').sub.2, Fab, Fv and Fd fragments; chimeric antibodies in which the Fc and/or Fr and/or CDR1 and/or CDR2 and/or light chain CDR3 regions have been replaced by homologous human or non-human sequences; chimeric F(ab').sub.2 fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or nonhuman sequences. The present invention also includes so-called single chain antibodies.

Thus, the invention involves polypeptides of numerous size and type that bind specifically to K41-glycated or K41-nonglycated CD59 molecules. These polypeptides may be derived also from sources other than antibody technology. For example, such polypeptide binding agents can be provided by degenerate peptide libraries which can be readily prepared in solution, in immobilized form or as phage display libraries. Combinatorial libraries also can be synthesized of peptides containing one or more amino acids. Libraries further can be synthesized of peptoids and non-peptide synthetic moieties.

Phage display can be particularly effective in identifying binding peptides useful according to the invention. Briefly, one prepares a phage library (using e.g. m13, fd, or lambda phage), displaying inserts from 4 to about 80 amino acid residues using conventional procedures. The inserts may represent, for example, a completely degenerate or biased array. One then can select phage-bearing inserts which bind to K41-glycated or K41-nonglycated CD59 molecules. This process can be repeated through several cycles of reselection of phage that bind to the CD59 molecules. Repeated rounds lead to enrichment of phage bearing particular sequences. DNA sequences analysis can be conducted to identify the sequences of the expressed polypeptides. The minimal linear portion of the sequence that binds to the CD59 molecules can be determined. One can repeat the procedure using a biased library containing inserts containing part of all of the minimal linear portion plus one or more additional degenerate residues upstream or downstream thereof. Yeast two-hybrid screening methods also may be used to identify polypeptides that bind to the CD59 molecules. Thus, K41-glycated CD59 molecules and K41-nonglycated CD59 molecules, or fragments thereof containing the glycation site, can be used to screen peptide libraries, including phage display libraries, to identify and select peptide binding partners of the K41-glycated or K41-nonglycated CD59 molecules.

As detailed herein, the foregoing antibodies and other binding molecules may be used for example to isolate and identify CD59 protein and/or K41-glycated and/or K41-nonglycated CD59 protein. The antibodies may be coupled to specific diagnostic labeling agents for imaging of the protein or fragment thereof. The antibodies may also be used for immunoprecipitation, immunoblotting CD59 and/or K41-glycated CD59 using standard methods known to those of ordinary skill in the art.

The invention also involves a variety of assays based upon detecting levels of K41-glycated CD59 in subjects. The assays include (1) characterizing the impact of blood sugar levels on glycation levels in a subject; (2) evaluating a treatment for regulating blood sugar levels in a subject; (3) selecting a treatment for regulating blood sugar levels in a subject; and (4) determining progression, progression or onset of a condition characterized by abnormal levels of glycated protein in a subject. Thus, subjects can be characterized, treatment regimens can be monitored, treatments can be selected and diseases can be better understood using the assays of the present invention. For example, the invention provides in one aspect a method for measuring the level of K41-glycated CD59 in a subject, which is a direct indicator of the level of the subject's glycemic control. The impact of blood sugar levels or glycation levels thus can be measured due to the positive correlation between the level of circulating blood glucose and the amount of glycation of endogenous CD59. The level of K41-glycated CD59 thus correlates with the level of glycemic control in the subject. Relatively low levels of K41-glycated CD59 reflect well-controlled circulating blood sugar levels and selectively high levels of K41-glycated CD59 reflect poorly controlled glycemic levels.

The assays described herein are carried out on samples obtained from subjects. As used herein, a subject is a human, non-human primate, cow, horse, pig, sheep, goat, dog, cat, or rodent. In all embodiments, human subjects are preferred. The samples used herein are any body tissue or body fluid sample obtained from a subject. Preferred are body fluids, for example, lymph, saliva, blood, urine, and the like. Blood and urine are preferred, urine being most preferred. It has been surprisingly discovered that glycated CD59 can be detected in urine, thereby obviating the need for a blood sample.

Particularly, important subjects to which the present invention can be applied are diabetic subjects.

The term "diabetic" as used herein, means an individual who, at the time the sample is taken, has a primary deficiency of insulin. The term diabetic includes, but is not limited to, individuals with juvenile diabetes (Type 1 diabetes), adult-onset diabetes (Type 2 diabetes), gestational diabetes, and any other conditions of insulin deficiency. The term "diabetic" is a term of art, known and understood by those practicing in the medical profession, a formal definition of which can be found in Harrison's Principles of Medicine (Harrisons, Vol 14, Principles of Internal Medicine, Eds. Fauci, A. S., E. Braunwald, K. J. Isselbacher, J. D. Wilson, J. B. Martin, D. L. Kasper, S. L. Hauser, D. L. Longo, McGraw-Hill, N.Y., 1999).

All of the assays described herein involve measuring levels of K41-glycated CD59. Levels of K41-glycated CD59 can be determined in a number of ways when carrying out the various methods of the invention. In one particularly important measurement, the level of K41-glycated CD59 is measured in relation to K41-nonglycated CD59. Thus, the measurement is a relative measure, which can be expressed, for example, as a percentage of total CD59. Another measurement of the level of K41-glycated CD59 is a measurement of absolute levels of K41-glycated CD59. This could be expressed, for example, in terms of grams per liter of body fluid. Another measurement of the level of K41-glycated CD59 is a measurement of the change in the level of K41-glycated CD59 over time. This may be expressed in an absolute amount or may be expressed in terms of a percentage increase or decrease over time.

Importantly, levels of K41-glycated CD59 are advantageously compared to controls according to the invention. The control may be a predetermined value, which can take a variety of forms. It can be a single cut-off value, such as a median or mean. It can be established based upon comparative groups, such as in groups having normal amounts of circulating insulin and groups having abnormal amounts of circulating insulin. Another example of comparative groups would be groups having a particular disease, condition or symptoms and groups without the disease, condition or symptoms. Another comparative group would be a group with a family history of a condition and a group without such a family history. The predetermined value can be arranged, for example, where a tested population is divided equally (or unequally) into groups, such as a low-risk group, a medium-risk group and a high-risk group or into quandrants or quintiles, the lowest quandrant or quintile being individuals with the lowest risk or amounts of glycated protein and the highest quandrant or quintile being individuals with the highest risk or amounts of glycated protein.

The predetermined value, of a course, will depend upon the particular population selected. For example, an apparently healthy population will have a different 'normal' range than will a population which is known to have a condition related to abnormal protein glycation. Accordingly, the predetermined value selected may take into account the category in which an individual falls. Appropriate ranges and categories can be selected with no more than routine experimentation by those of ordinary skill in the art. By abnormally high it is meant high relative to a selected control. Typically the control will be based on apparently healthy normal individuals in an appropriate age bracket.

In measuring the relative amount of K41-glycated CD59 to K41-nonglycated CD59, those of ordinary skill in the art will appreciate that the relative amount may be determined by measuring either the relative amount of K41-glycated CD59 or the relative amount of K41-nonglycated CD59. In other words, if 90% of an individual's CD59 is K41-nonglycated CD59, then 10% of the individual's CD59 will be K41-glycated CD59. Thus, measuring the level of K41-glycated CD59 may be carried out by measuring the relative amount of K41-nonglycated CD59.

It will also be understood that the controls according to the invention may be, in addition to predetermined values, samples of materials tested in parallel with the experimental materials. Examples include samples from control populations or control samples generated through manufacture to be tested in parallel with the experimental samples.

The various assays used to determine the levels of K41-glycated CD59 include: binding assays, such as described in the examples below; specific binding assays, such as using materials which bind specifically to K41-glycated CD59; gel electrophoresis; NMR; and the like. Immunoassays may be used according to the invention including sandwich-type assays, competitive binding assays, one-step direct tests and two-step tests such as described in the examples.

As mentioned above, it is also possible to characterize blood sugar levels by monitoring changes in the absolute or relative amounts of glycated CD59 over time. For example, it is expected that an increase in glycated CD59 correlates with increasing dysregulation of glycemic levels. Accordingly one can monitor glycated CD59 levels over time to determine if glycemic levels of a subject are changing. Changes in relative or absolute glycated CD59 of greater than 0.1% may indicate an abnormality. Preferably, the change in glycated CD59 levels, which indicates an abnormality, is greater than 0.2%, greater than 0.5%, greater than 1.0%, 2.0%, 3.0%, 4.0%, 5.0%, 7.0%, 10%,. 15%, 20%, 25%, 30%, 40%, 50%, or more. Reductions in amounts of glycated CD59 over time may indicated improved glycemic control.

The invention in another aspect provides a diagnostic method to determine the effectiveness of treatments for abnormal glycemic levels. The "evaluation of treatment" as used herein, means the comparison of a subject's levels of K41-glycated CD59 measured in samples collected from the subject at different sample times, preferably at least one day apart. The preferred time to obtain the second sample from the subject is at least one day after obtaining the first sample, which means the second sample is obtained at any time following the day of the first sample collection, preferably at least 12, 18, 24, 36, 48 or more hours after the time of first sample collection.

The comparison of levels of K41-glycated CD59 in two or more samples, taken on different days, is a measure of level of the subject's glycemic control and allows evaluation of the treatment to regulate blood sugar levels. The comparison of a subject's levels of K41-glycated CD59 measured in samples obtained on different days provides a measure of glycemic control to determine the effectiveness of any treatment to regulate blood sugar levels.

As will be appreciated by those of ordinary skill in the art, the evaluation of the treatment also may be based upon an evaluation of the symptoms or clinical end-points of the associated disease, such as the vascular complications of diabetes. Thus, the methods of the invention also provide for determining the regression, progression or onset of a condition which is characterized by abnormal levels of glycated protein, including those characterized by abnormal levels of K41-glycated CD59. In some instances, the subjects to which the methods of the invention are applied are already diagnosed as having a particular condition or disease. In other instances, the measurement will represent the diagnosis of the condition or disease. In some instances, the subjects will already be undergoing drug therapy for regulating blood sugar levels, while in other instances the subjects will be without present drug therapy for regulating blood sugar levels.

According to still another aspect of the invention, a method is provided for treating a subject to reduce the risk of a disorder associated with abnormally-high levels of K41-glycated CD59. The method involves selecting and administering to a subject who is known to have an abnormally-high level of K41-glycated CD59, an agent for treating the disorder. Preferably, the agent is an agent for reducing K41-glycated CD59 levels and is administered in an amount effective to reduce K41-glycated CD59 levels.

In this aspect of the invention, the treatments are based upon selecting subjects who have unwanted, elevated levels of K41-glycated CD59. Such subjects may already be receiving a drug for regulating blood sugar levels, but, according to the invention, are now candidates for an elevated level of the drug based upon the presence of the elevated levels of K41-glycated CD59. It may be appropriate according to the invention to alter a therapeutic regimen for a subject, based upon the measurement of the level of K41-glycated 59. This can be understood in connection with treatment of diabetics. Diabetics are treated in at least three different ways. Some diabetics are treated only with non-drug therapy, such as exercise and diet. Other diabetics are treated with oral drug therapy, but not with insulin which is injected. Finally, some diabetics are treated with insulin or analogs of insulin by injection. According to the present invention, as a result of determining an elevated level of K41-glycated CD59, an individual undergoing only non-drug therapy may be a candidate for drug therapy as a result of the K41-glycated CD59 test. Likewise, a subject receiving only oral drug therapy, may be a candidate for an insulin-based injectable therapy, due to the K41-glycated CD59 test. Finally, a subject may be free of any present treatment but may be a candidate for blood sugar level regulating treatment as a result of the K41-glycated CD59 test. Thus, subjects may be selected and treated with elevated levels of the same drugs or with different therapies as a result of the assays of the invention.

According to the present invention, some of the subjects are free of symptoms otherwise calling for treatment with a particular therapy. This means that absent the K41-glycated CD59 test, the subject would not according to convention as of the date of the filing of the present application have symptoms calling for treatment with a particular therapy. It is only as a result of the measuring the level of K41-glycated CD59 that the subject becomes a candidate for treatment with the therapy.

Drug therapies for regulating blood sugar levels include oral therapies with hypoglycemic agents an/or oral anti-diabetic agents, injectable therapies, and the like. Non-drug therapies for regulating blood sugar level include, but are not limited to, diatetic and/or exercise control measures.

Diet and exercise alterations include, but are not limited to, reducing caloric intake, and/or increasing fiber intake, and/or decreasing fat intake, and/or increasing exercise level.

Oral drug therapies for regulating blood sugar levels include hypoglycemic agents that may include, but are not limited to:

Acarbose; Acetohexamide; Chlorpropamide; Darglitazone Sodium: Glimepiride; Glipizide; Glyburide, Repaglinide; Troglitazone; Tolazamide; Tolbutamide.

Oral drug therapies for regulating blood sugar levels include antidiabetic agents that may include but are not limited to:

Acarbose, Acetohexamide; Buformin; Butoxamine Hydrochloride ; Camiglibose; Chlorpropamide; Ciglitazone; Englitazone Sodium; Etoformin Hydrochloride; Gliamilide; Glibomuride; Glicetanile Gliclazide Sodium; Gliflumide; Glipizide; Glucagon; Glyburide; Glyhexamide; Glymidine Sodium; Glyoctamide; Glyparamide; Insulin; Insulin, Dalanated; Insulin Human; Insulin Human, Isophane; Insulin Human Zinc; Insulin Human Zinc, Extended; Insulin, Isophane; Insulin Lispro; Insulin, Neutral; Insulin Zinc; Insulin Zinc, Extended; Insulin Zinc, Prompt; Linogliride; Linogliride Fumarate; Metformin; Methyl Palmoxirate; Palmoxirate Sodium; Pioglitazone Hydrochloride; Pirogliride Tartrate; Proinsulin Human; Repaglinide; Seglitide Acetate; Tolazamide; Tolbutamide; Tolpyrramide; Troglitazone; Zopolrestat.

Injectable therapies for regulating blood sugar levels may include, but are not limited to:

Fast-Acting Insulin:
Insulin Injection: regular insulin; Prompt Insulin Zinc Suspension; Semilente® insulin. These categories include preparations such as: Humalog® Injection; Humulin® R; Iletin II; Novolin R, Purified Pork Regular Insulin; Velosulin BR Human Insulin Intermediate-acting Insulin:
Isophane Insulin Suspension: NPH insulin, isophane insulin; Insulin Zinc Suspension Lente® Insulin. These categories include preparations such as: Humulin® L; Humulin® R; Humulin® N NPH; Iletin® II, Lente®; Iletin® II, NPH; Novolin® L, Novolin® N, Purified Pork Lente® insulin, Purified Pork NPH isophane isulin. Intermediate and Rapid-acting Insulin Combinations:
Human Insulin Isophane Suspension/Human Insulin Injection;. This category includes preparations such as: Humulin® 50/50; Humulin® 70/30; Novolin® 70/30 Long-acting Insulin:
Protamine Zinc Insulin Suspension; Extended Insulin Zinc Suspension. These categories include preparations such as: Ultralente® Insulin, Humulin® U.

Reducing the risk of a disorder associated with abnormally high levels of K41-glycated CD59 means using treatments and/or medications to reduce K41-glycated CD59 levels, therein reducing, for example, the subject's risk of vascular complications including but not limited to: diabetic nephropathy, diabetic retinopathy, macro-vascular disease, micro-vascular disease, and diabetic neuropathy.

In a subject determined to have an abnormally high level of K41-glycated CD59, an effective amount is that amount effective to reduce K41-glycated CD59 levels in the subject. A response can, for example, also be measured by determining the physiological effects of the hypoglycemic, antidiabetic, or insulin composition, such as the decrease of disease symptoms following administration of the hypoglycemic, antidiabetic, or insulin. Other assays will be known to one of ordinary skill in the art and can be employed for measuring the level of the response. The amount of a treatment may be varied for example by increasing or decreasing the amount of a therapeutic composition, by changing the therapeutic composition administered, by changing the route of administration, by changing the dosage timing and so on. The effective amount will vary with the particular condition being treated, the age and physical condition of the subject being treated, the severity of the condition, the duration of the treatment, the nature of the concurrent therapy (if any), the specific route of administration, and the like factors within the knowledge and expertise of the health practitioner. For example, an effective amount can depend upon the degree to which an individual has abnormally elevated levels of K41-glycated CD59.

An "effective amount" of a drug therapy is that amount of a hypoglycemic, antidiabetic, or insulin or insulin analog that alone, or together with further doses, produces the desired response, e.g. reduction of glycemic level or K41-glycated CD59 levels.

In the case of treating a particular disease or condition the desired response is inhibiting the progression of the disease or condition. This may involve only slowing the progression of the disease temporarily, although more preferably, it involves halting the progression of the disease permanently. This can be monitored by routine diagnostic methods known to one of ordinary skill in the art for any particular disease. The desired response to treatment of the disease or condition also can be delaying the onset or even preventing the onset of the disease or condition.

Such amounts will depend, of course, on the particular condition being treated, the severity of the condition, the individual patient parameters including age, physical condition, size and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the hypoglycemic, antidiabetic, or insulin composition (alone or in combination with other therapeutic agents) be used, that is, the highest safe dose according to sound medical judgment. It will be understood by those of ordinary skill in the art, however, that a patient may insist upon a lower dose or tolerable dose for medical reasons, psychological reasons or for virtually any other reasons.

The pharmaceutical compositions used in the foregoing methods preferably are sterile and contain an effective amount of hypoglycemic, antidiabetic, or insulin for producing the desired response in a unit of weight or volume suitable for administration to a patient.

The doses of hypoglycemic, antidiabetic, or insulin administered to a subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits.

Various modes of administration will be known to one of ordinary skill in the art which effectively deliver the hypoglycemic, antidiabetic, or insulin to a desired tissue, cell or bodily fluid. Preferred methods for administering the hypoglycemic and antidiabetic are oral. The preferred method of administering insulin is by injection. Administration includes: topical, intravenous, oral, intracavity, intrathecal, intrasynovial, buccal, sublingual, intranasal, transdermal, intravitreal, subcutaneous, intramuscular and intradermal administration. The invention is not limited by the particular modes of administration disclosed herein. Standard references in the art (e.g., *Remington's Pharmaceutical Sciences*, 18th edition, 1990) provide modes of administration and formulations for delivery of various pharmaceutical preparations and formulations in pharmaceutical carriers. Other protocols which are useful for the administration of hypoglycemic, antidiabetic, or insulin will be known to one of ordinary skill in the art, in which the dose amount, schedule of administration, sites of administration, mode of administration (e.g., intra-organ) and the like vary from those presented herein.

Administration of hypoglycemic, antidiabetic, or insulin to mammals other than humans, e.g. for testing purposes or veterinary therapeutic purposes, is carried out under substantially the same conditions as described above. It will be understood by one of ordinary skill in the art that this invention is applicable to both human and animal diseases which can be treated by hypoglycemic, antidiabetic or insulin. Thus this invention is intended to be used in husbandry and veterinary medicine as well as in human therapeutics.

When administered, the pharmaceutical preparations of the invention are applied in pharmaceutically-acceptable amounts and in pharmaceutically-acceptable compositions. The term "pharmaceutically acceptable" means a non-toxic material that does not interfere with the effectiveness of the biological activity of the active ingredients. Such preparations may routinely contain salts, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts. Preferred components of the composition are described above in conjunction with the description of the hypoglycemic, antidiabetic, or insulin compositions of the invention.

A hypoglycemic, antidiabetic, or insulin composition may be combined, if desired, with a pharmaceutically-acceptable carrier. The term "pharmaceutically-acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the hypoglycemic, antidiabetic, or insulin, and with each other, in a manner such that there is no interaction which would substantially impair the desired pharmaceutical efficacy.

The pharmaceutical compositions may contain suitable buffering agents, as described above, including: acetate, phosphate, citrate, glycine, borate, carbonate, bicarbonate, hydroxide (and other bases) and pharmaceutically acceptable salts of the foregoing compounds.

The pharmaceutical compositions also may contain, optionally, suitable preservatives, such as: berizalkonium chloride; chlorobutanol; parabens and thimerosal. The pharmaceutical compositions may conveniently be presented in unit dosage form and may be prepared by any of the methods well-known in the art of pharmacy. All methods include the step of bringing the active agent into association with a carrier which constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for oral administration may be presented as discrete units, such as capsules, tablets, lozenges, each containing a predetermined amount of the active compound. Other compositions include suspensions in aqueous liquids or non-aqueous liquids such as a syrup, elixir or an emulsion.

Compositions suitable for parenteral administration conveniently comprise hypoglycemid, antidiabetic, or insulin. This preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono-or di-glycerides. In addition, fatty acids such as oleic acid may be used in the preparation of injectables. Carrier formulation suitable for oral, subcutaneous, intravenous, intramuscular, etc. administrations can be found in *Remington's Pharmaceutical Sciences*, Mack Publishing Co., Easton, Pa.

The application of the invention to a diabetic subject under treatment with an oral blood sugar regulating agent and otherwise free of symptoms calling for any oral blood sugar regulating agent, as used herein means a subject treated with oral blood sugar regulators whose glycemic-control levels appear normal based on standard diagnostic criteria, including but not limited to measurement of glycated hemoglobin levels.

The application of the invention to a diabetic subject under treatment with insulin (including analogs thereof) and otherwise free of symptoms calling for any insulin, as used herein means a subject treated with insulin whose glycemic-control levels appear to be normal based on standard diagnostic criteria, including but not limited to measurement of glycated hemoglobin levels.

Dosages of blood sugar regulating agents are well-known to those of ordinary skill in the art and documented in the literature.

Referring to FIG. 1, a kit according to the invention is shown. The kit 11 includes a package 15 housing a container 17 which contains an agent for determining the level of K41-glycated CD59 in a sample. The kit also includes a control 19. The kit also may further comprise instructions 21, as described above. The instructions typically will be in written form and will provide guidance for carrying-out the assay embodied by the kit and for making a determination based upon that assay.

EXAMPLES

Example I

Introduction

To investigate whether in vitro glycation of human CD59 inhibits its homologous restriction activity a functional assay of glycated CD59 was performed. A 10% cell suspension of guinea pig erythrocytes (GPE) was incubated with purified CD59 previously exposed for different time intervals to the glycating sugars glucose (0.5M) or ribose (0.5M), or to non-glycating sorbitol (0.5M) to control for the high osmolarity of the medium. The sensitivity of the GPE to human membrane attack complex (MAC) was tested using purified human C5b6 and C7, C8 and C9 (Halperin et al, 1993a) The number of CD59 molecules incorporated per GPE was determined with 1251-CD59 before and after glycation with ribose.

Methods

CD59 purification: CD59 from urine was isolated by anion exchange chromatography using a DEAE protein-Pak HR 8 column (Waters Corp., Milford, Mass.) as described in Davies et al, 1998. CD59 from butanol extracts of RBC and lysates of CHO cells was purified by immunoaffinity chromatography (see: Davies et al, 1998, Hughes et al, 1992, and van den Berg et al, 1993) using the monoclonal rat anti-human CD59 antibody YTH 53.1 (Serotec Inc. Raleigh, N.C.), as in Fletcher, et al., 1994. Protein concentration was estimated by the micro-BCA protein assay (Pierce Chemical Co. Rockford, Ill.). Western blots were performed on proteins separated by SDS-PAGE using the Supersignal detection system (Pierce Chemical Co.).

Functional Activity Assays. Hemolysis Protection Assay

Activity of purified CD59 and its mutants before and after glycation was determined by a hemolysis protection assay using guinea pig erythrocytes (GPE) exposed to the terminal complement proteins C5b6, C7, C8 and C9 to form the MAC, as described in Benzaquen, et al, 1994 and Halperin et al., 1993b. In this assay, ~10-3 unit of human C5b6 is required to lyse 50% of a GPE cell suspension (one unit is the amount of C5b6 required to lyse 50% of a human RBC suspension [Haperin et al, 1993a]). The activity of purified CD59 was defined as the difference between the percent lysis of the unprotected GPE minus the percent lysis of the CD59-protected GPE.

In vitro glycation: Purified CD59 (10-30 μg/ml) was incubated for different time intervals at 37° C. in 0.5 M of either reducing monosaccharides (glucose, ribose, or glucose-6-phosphate) or the non-glycating sorbitol to control for potential osmotic effects.

Incorporation of CD59 into GPE: Purified CD59 was iodinated with 1251 (NEN® Life Science Products Inc. Boston, Mass.) using Iodobeads (Pierce Chemical Co.). Iodination of CD59 did not affect either its homologous restriction activity or its sensitivity to glycation-inactivation. After incubation of GPE with 1251-CD59, the cells were washed extensively to remove unbound CD59, lysed and the radioactivity incorporated was measured in a gamma counter. Using standard methods, the number of CD59 molecules incorporated per GPE was calculated from the specific activity of the 1251-CD59 preparation (150 cpm/ng) and the hematocrit of the GPE suspension.

Results

Figure 2:
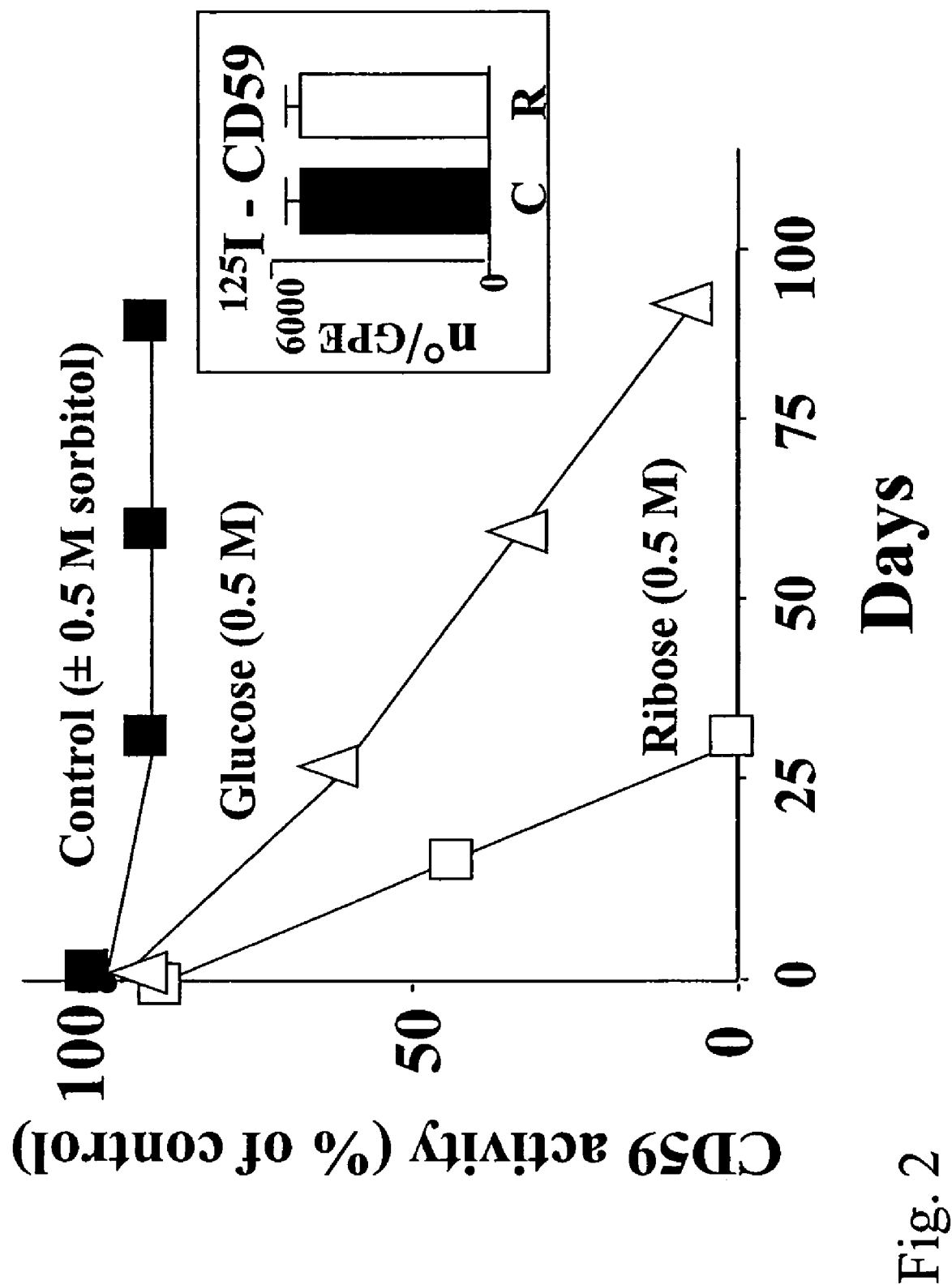
FIG. 2 is a graph indicating CD59 activity as a percent of control activity for a cell suspension of GPE incubated with purified CD59 previously exposed for different time intervals to the glycating sugars glucose (open triangles, 0.5M) or ribose (open squares; 0.5M), or to non-glycating sorbitol (closed squares, 0.5M). Data points represent the mean of triplicate determinations (SEM are smaller than data points). Figure is representative of experiments run three times with comparable results. Inset shows the number of CD59 molecules incorporated per GPE as determined with $^{125}$I-CD59 before (C) and after (R) glycation with ribose.

Glycation abrogates the homologous restriction activity of human CD59. The results, illustrated in FIG. 2, demonstrate that incubation of CD59 with the glycating sugars glucose and ribose significantly reduce the CD59 activity.

Example 2

Introduction

To determine the location of the site that when glycated inactivates the CD59 molecule, replacement by site-directed mutagenesis of either K41 or H44 was performed. Wild type (WT) and CD59 mutants Gln-41 and Gln-44 were expressed in CHO cells and purified by affinity chromatography. The activity of the mutant CD59 molecules was tested in the GPE hemolytic assay before and after glycation with ribose for different time intervals.

Methods

Expression and purification assays: Using standard methods, wild-type and mutant CD59 cDNAs were subcloned into the mammalian expression vector pSVK3 (Amersham Pharmacia Biotech Inc. Piscataway, N.J.) and transfected into CHO cells together with the selection marker pBABE, which confers resistance to puromycin. Expression and functionality of the WT and mutant CD59 in the puromycin resistant clones were tested by Western blot analysis, inimunohistochemistry in non-permeabilized cells using the YTH 53.1 antibody and a Texas Red conjugated secondary antibody, and a functional dye release assay, which measures protection against human complement, as described in Zhao et al., 1991.

Site-directed Mutagenesis: Plasmid pK562-3 containing the cDNA of human CD59 (Philbrick, et al., 1990) was obtained from ATCC. Site-directed mutagenesis to substitute residue K41 or H44 for glutamine (Gln) was performed using the Altered Sites 11 system (Promega Corp. Madison, Wis.). The mutagenic primers used were 5'-GTC GTT GAA ATT ACA ATG CTC AAA CTG CCA ACA CTT-3' (SEQ ID NO.: 2) for the Gln-41 substitution, and 5'-GTT GAA ATT GCA CTG CTC AAA CTT CCA-3' (SEQ ID NO.: 3) for the Gln-44 mutation. Successful mutagenesis was confirmed by sequencing using standard methods.

For description of CD59 *Purification, In vitro Glycation, and Hemolysis Protection Assay*: See Example 1, Methods.

Results

Replacement by site-directed mutagenesis of either K41 or H44 abolished the sensitivity of human CD59 to glycation-inactivation confirming that the K41-H44 motif constitute a glycationinactivation site. Results of the GPE lysis assay and the CD59 activity assay are illustrated in FIG. 3.

Example 3

Introduction

To determine whether glycation of human endothelial cells and human red blood cells (RBC) results in the inactivation of CD59, an experiment was designed to detect whether glycation would render human endothelial cells and human red blood cells (RBC) more sensitive to MAC mediated growth factor release or MAC-mediated lysis. Both the endothelial cells and the RBC were glycated and exposed to purified terminal complement components C5b6, C7, C8, and C9 to form the MAC and the mitogenic activity in the conditioned medium was measured.

Methods

Glycation of RBC: A 10% RBC suspension was incubated with or without ribose (50 mM) for 48 hours at room temperature, followed by 20 min incubation with cyanoborohydride (20 mM). Cell volume was then adjusted by the nystatin procedure (described in Halperin, et al, 1987) and the osmotic fragility of the cell suspension was measured by standard procedures. To ascertain that differential sensitivity to lysis was not caused by an increased osmotic fragility of RBC exposed to glycating agents, RBC were only used when average cell volume and osmotic fragility were similar to that of control cells.

Glycation of HUVEC: Confluent second passage HUVEC were incubated with or without ribose (50 mM) for 24 hr (37°, 5% C02) followed by 20 min incubation with cyanoborohydride (20 mM). Cells were then exposed to purified terminal complement proteins to form the MAC, aliquots of conditioned media separated to test for mitogenic activity in indicator quiescent 3T3 cells, as described in Benzaquen et al, 1994.

RBC and HUVEC Analysis

To avoid confounding effects of colloidosmotic swelling caused by the glycating agent, cell volume was adjusted in all cells, glycated and non-glycated prior to assaying for sensitivity to MAC-induced lysis (Halperin, et al, 1987). After volume adjustment, aliquots of glycated and non-glycated cells were separated for rescue with purified CD59 (4 μg), exposure to neutralizing anti-CD59 antibody (YTH53.1) or both, and then exposed to purified C5b6, C7, C8 and C9 to form the MAC.

Results

The data indicate that glycation of the endothelial calls and RBC makes them more sensitive to MAC-mediated growth factor release and MAC-mediated lysis (see FIG. 4). Results are expressed as the ratio of mitogenic activity released into the conditioned media in the presence or absence of MAC.

Example 4

Introduction

To determine whether glycated CD59 is present in human urine, which indicates that glycation occurs in vivo, urine from a nondiabetic subject was concentrated, fractionated, and tested for the presence of CD59 using an anti-CD59 specific antibody. The CD59 positive fractions were then purified further and probed with an antibody that specifically recognizes the reduced ketoamine of glycated lysine residues and binds to the glycated region of CD59, to determine whether glycated CD59 was present in the sample.

Methods

For details of the *CD59 Purification*, see Example 1, Methods section. *Immunoblotting with Anti-hexitol-lysine Antibody* was performed using standard procedures as described in Myint, et al, 1995.

Results

The CD59 isolated from a non-diabetic subject was immunoblotted with the anti-hexitol-lysine antibody, which recognizes the glycated CD59. The results illustrated in FIG. 5 demonstrate that glycated CD59 is present in human urine.

Example 5

Introduction

Following the identification of glycated CD59 in human urine, the levels present in urine were measured to determine whether levels of glycated CD59 correlate with levels of glycated hemoglobin (HbA I c) in diabetic and nondiabetic subjects. Concentrated human urine from either normoglycemic or hyperglycemic (diabetic) individuals was separated by anion exchange chromatography, and a CD59-positive fractions were immunoprecipitated with a monoclonal anti-CD59 antibody. The antibody was used because it binds to an epitope distant from the K41-K44 putative glycation motif on CD59 and was, therefore expected to precipitate both glycated and non-glicated CD59. An aliquot of the immunoprecipitate was separated by SDS-PAGE and blotted with the monoclonal anti-CD59 antibody YTH53.1.

Methods

For detail of *CD59 Purification and Quantification* see Example 1, Methods section.

Measurements of HbAlc were performed using standard procedures at the Joslin Diabetic Center (Boston, Mass.).

For details of *Immunoblotting with Anti-hexitol-lysine Antibody*, see Example 4, Methods section.

Results

Comparison of the levels of glycated CD509 and glycated hemoglobin from diabetic and nondiabetic subjects indicate that the levels of glycated CD59 correlate with the levels of glycated hemoglobin (see FIG. 5).

REFERENCES

Halperin, J. A. et al., *J. Clin. Invest.* 91, 1974-1978 (1993)
Benzaquen, L. R., et al., *J. Exp. Med* 179, 985-992 (1994)
Fletcher, C. M., et al., *Structure* 2, 185-199 (1994)
Myint, T. et al., *Biochim. Biophys. Acta* 1272, 73-79 (1995)
Davies, A., et al., *J. Exp. Med.* 170, 637-654 (1989)
Hughes, T. R., et al., *Biochem. J.*, 284, 169-176 (1992)
van den Berg., C. W., et al., *Immunology* 78, 349-357 (1993)
Philbrick, W. M., et al., *Eur. J. Immunol.* 20, 87-92 (1990)
Zhao, J., et al., *J. Biol. Chem.* 266, 13418-13422 (1991)
Halperin, J. A., et al., *Blood* 81, 200-205 (1993D)
Halperin, J. A. et al., *J. Clin. Invest* 80, 128-137 (1987)

It will be understood that those of ordinary skill in the art that the foregoing represents only certain embodiments of the invention. It will be understood that equivalents of the foregoing are intended to be encompassed within the following claims.

SEQUENCE LISTING

```
<160> NUMBER OF SEQ ID NOS: 3

<210> SEQ ID NO 1
<211> LENGTH: 15
<212> TYPE: PRT
<213> ORGANISM: Homo sapiens

<400> SEQUENCE: 1

Tyr Asn Lys Ala Trp Lys Phe Glu His Ala Asn Phe Asn Asp Cys
1               5                   10                  15

<210> SEQ ID NO 2
<211> LENGTH: 36
<212> TYPE: DNA
<213> ORGANISM: Homo sapiens

<400> SEQUENCE: 2
gtcgttgaaa ttacaatgct caaactgcca acactt                           36

<210> SEQ ID NO 3
<211> LENGTH: 27
<212> TYPE: DNA
<213> ORGANISM: Homo sapiens

<400> SEQUENCE: 3
gttgaaattg cactgctcaa acttcca                                     27
```

TABLE 1

Sequence Information

AMINO ACID SEQUENCES

SEQ ID NO:1 YNKAWKFEHANFNDC

NUCLEIC ACID SEQUENCES

SEQ ID NO:2: GTCGTTGAAATTACAATGCTCAAACTGCCAACACTT
SEQ ID NO:3: GTTGAAATTGCACTGCTCAAACTTCCA

We claim:

1. A kit for measuring the level of glycated CD59 in a sample, the kit comprising a package comprising an isolated first antibody or antigen binding fragment thereof that binds specifically to an epitope comprising a glycated K41 of a K41- glycated CD59 or binds specifically to an epitope comprising a non-glycated K41 of a non K41-glycated CD59, and an isolated control second antibody or antigen-binding fragment thereof for recognizing the total amount of CD59 in the sample.

2. The kit of claim 1, wherein the control second antibody is an antibody that binds to non-glycated CD59 and glycated CD59.

3. The kit of claim 1, further comprising instructions for using the antibodies or antigen binding fragments thereof to detect the level of glycated CD59 in the sample.

4. The kit of claim 3, wherein the instructions comprise instructions for determining the level of glycated CD59 in a fluid sample.

5. The kit of claim 4, wherein the instructions comprise instructions for determining the level of glycated CD59 in a fluid sample comprising blood.

6. The kit of claim 4, wherein the instructions comprise instructions for determining the level of glycated CD59 in a fluid sample comprising urine.

7. The kit of claim 4, wherein the instructions comprise instructions for determining the level of glycated CD59 in a fluid sample comprising saliva.

8. The kit of claim 3, wherein the instructions comprise instructions for determining the level of glycated CD59 in a tissue sample.

9. The kit of claim 3, wherein the instructions comprise instructions for determining a level of glycated CD59 measured as a percentage of the total CD59 in the sample.

10. The kit of claim 3, wherein the instructions comprise instructions for determining a level of glycated CD59 that is the level of K41-glycated CD59 relative to the level of non-glycated CD59 in the sample.

11. The kit of claim 1, wherein one or more of the antibodies or antigen-binding fragments thereof is detectably labeled.

12. The kit of claim 1, wherein one or more of the antibodies is a monoclonal antibody.

13. The kit of claim 1, wherein one or more of the antibodies is a polyclonal antibody.

* * * * *